United States Patent [19]

Ninan et al.

[11] Patent Number: 4,742,815
[45] Date of Patent: May 10, 1988

[54] COMPUTER MONITORING OF ENDOSCOPE

[76] Inventors: Champil A. Ninan; Abraham C. Ninan, both of 707 McArthur Rd., Fayetteville, N.C. 28301-9116

[21] Appl. No.: 815,455

[22] Filed: Jan. 2, 1986

[51] Int. Cl.⁴ .............................................. A61B 1/00
[52] U.S. Cl. ...................................................... 128/4
[58] Field of Search ..................................... 128/4–8, 128/303.1, 303.13–303.17, 395–398

[56] References Cited

U.S. PATENT DOCUMENTS

| | | | |
|---|---|---|---|
| 4,231,372 | 11/1980 | Newton | 128/303.17 |
| 4,253,447 | 3/1981 | Moore et al. | 128/6 |
| 4,292,961 | 10/1981 | Kawashima | 128/6 |
| 4,343,300 | 8/1982 | Hattori | 128/6 |
| 4,590,923 | 5/1986 | Watanabe | 128/6 |
| 4,593,313 | 6/1986 | Nagasaki et al. | 128/6 |

*Primary Examiner*—Max Hindenburg
*Attorney, Agent, or Firm*—Rhodes, Coats and Bennett

[57] ABSTRACT

An endoscope is modified so it can be connected to a computer. Thus all the movements of the said endoscope is monitored and displayed on the computer screen in color graphic form. When surgery is performed using the said endoscope there are limits within which cutting away of the diseased tissue is safe. Surgery beyond these safe limits can cause dangerous consequences to the patient. These safe limits are preset. During surgery the position of the cutting element of the said endoscope is continuously monitored and displayed. When any of these limits are transgressed and the cutting current is about to be switched on then an alarm by the computer alerts the surgeon. Events occurring during surgery are recorded on the computer disc for future reference. The importance of this is exact and continuous monitoring of the cutting element and recording the surgery for future playback and study.

18 Claims, 6 Drawing Sheets

COMPUTER MONITORING OF ENDOSCOPE

TECHNICAL FIELD

The present invention relates in general to computer monitoring of the exact position of an endoscope, sound alarms as set, and record events occurring during the procedure.

BACKGROUND OF THE INVENTION

Numerous endoscopes are now being used to examine and operate upon various parts of a patient. An endoscope called the Resectoscope has made a most distressing operation called Open Prostatectomy into the finest of all surgeries because it is painless and minimises blood loss. The above statement is qualified 'when done well' because complications can occur and make this into the worst of all surgeries.

The diseased prostate obstructs the patients urinary passage just as it leaves the urinary bladder. In this surgery called 'Trans Urethral Resection of the Prostate' the prostate is cut into pieces under vision and removed through the said resectoscope.

The prostate gland lies within three boundries namely the bladder neck above, the verumontanum below, and its outer boundery being its capsule. Resecting (cutting) within these limits is safe but if any cutting is done beyond these limits then dangerous complications can occur. Such complications occur when a trainee surgeon operates or if a large prostate is removed by a less experienced surgeon. Reasons for this are that only the operating surgeon can see through the endoscope and recognizing the safe limits becomes difficult especially when the field of vision is obscured by heavy bleeding.

Displaying the prostate on the computer screen and continuous display of the cutting element of its every move will enable the senior surgeon to know exactly what the trainee is doing.

Another important thing is that the gland needs to be removed completely. Any remaining tissue can grow and cause obstruction later. In this invention as soon as the prostatic capsule is reached this is marked and displayed on the computer screen in color. In the end one look at the screen will show the surgeon if any tissue has been left behind.

Serious complications occur if one perforates the prostatic capsule. Many blood vessels are present here and when cut into causes much bleeding and possible shock from blood loss. Also if a large vein is cut then the irrigating fluid enters the blood circulation through the cut vein causing hyponatremia (dilution hence reduction of sodium content of blood). The patient then looses consciousness and goes into shock.

The commonest way this happens is as follows: The surgeon cuts away the prostate from bladder neck to a distance of say 2 centimeters and reaches prostatic capsule here. Then when he begins cutting from this point beyond for another 2 centimeters inadvertantly he cuts an area where capsule has already been reached. The present invention will prevent this by an alarm.

One of the most distressing complications occur when resection is done beyond the verumontanum. The result is damage to the external urethral sphincter causing incontinence. Inability to control urine keeps him continuously wet. The present invention alerts the physician and this complication can now be avoided.

The computer starts timing the surgery and displays the time. When a capsule perforation occurs by mistake this event can be marked and the time interval between this occurrence and the end of surgery is important because the longer this 'perforation time' the greater the amount of irrigation fluid can leak outside the prostate and into the blood stream. This time is recorded.

It is possible to record an operation using a video camera but using this is cumbersome because of size and it is expensive. We will now be able to record events occuring during the said procedure in a cheap computer disc and display it whenever desired. Such reliable documentation of what the physician did will become important in the future.

DISCLOSURE OF INVENTION

During examination and surgery using an endoscope, the instrument is moved in and out of the body cavity. The cutting element of the said endoscope is also being moved in and out in relation to the endoscope sheath. Movement of the whole instrument also takes place in the circular plane. All these movements must be monitored in relation to landmarks in the examining organ. Once this is done then alarms can be set as warning whenever the predetermined landmarks are transgressed. In an endoscope where cutting is done the most important time to monitor is when the cutting current is switched on and the cutting element is moved to cut tissue that comes in contact with it. It is during this time that if preset boundaries are transgressed that alarms are to be sounded and if necessary switch off the cutting current.

In order to accomplish this above mentioned objects movement of the said endoscope in its various planes must be converted by a transducer to something that the computer will be able to receive, understand and act according to information received. Movement can thus be converted by using transducers like resistance, capacitance, inductance, current, voltage, light intensity, frequency rate, or time of reflected frequency.

Changing resistance with change in position of the endoscope was selected in the present model. Movement in three planes need to be monitored in this instance: 1. In and out plane. 2. The position of the cutting element in relation to the endoscope sheath. 3. Circular plane. Thus three potentiometers are used. Each varies resistance when movement occurs in its particular plane. Change of resistance and current due to movement is fed to an analog to digital converter (ADC) chip. This converts analog variations to ditital numbers. This is connected to the computer central processing unit (CPU) through a buffer chip. By programming the computer acts as programed upon receiving information.

BRIEF DESCRIPTION OF DRAWINGS

The above mentioned purposes and descriptions of the invention will be clear by reference to the following drawings wherein.

DETAILED DESCRIPTION OF THE PREFERRED EMBODIMENT

Discussion will be in the following order:
1. Description of prostate.
2. Description of endoscope.
3. Movements of endoscope.
4. Interfacing the endoscope to computer.
5. Computer programing.

Figure 1:
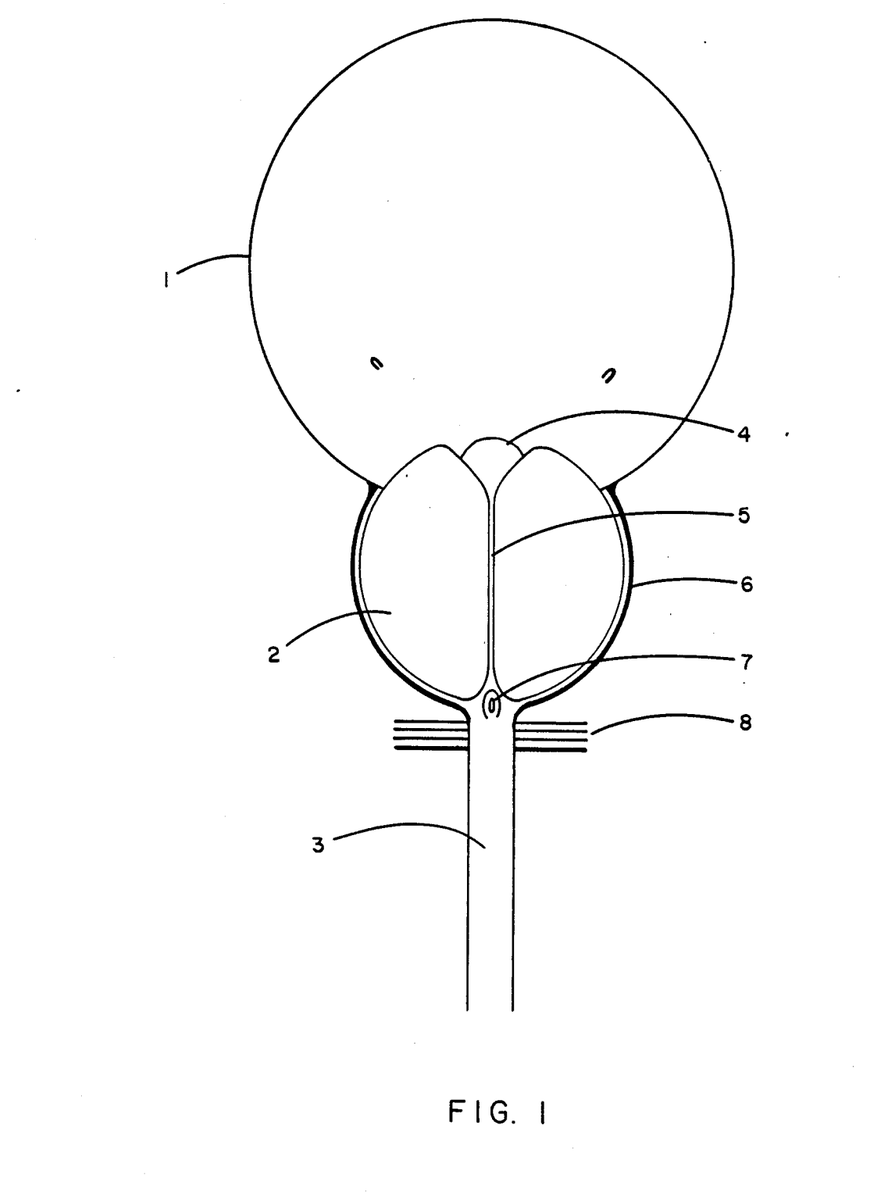
FIG. 1 is a view of the bladder, prostate, and urethra.

Referring to FIG. 1 the urinary bladder 1 is seen. Below this is the prostate gland 2 and this leads to the rest of the urinary passage called the urethra 3.

We are interested in the prostate 2. The upper limit of the prostate 2 is the bladder neck 4. Through the center of the prostate 2 passes the prostatic urethra 5. In disease the prostate 2 enlarges and compreses the prostatic urethra 5 as shown in this diagram. The lower end of the prostate 2 is marked by the veru 7 (more fully called the verumontanum). This is the most important landmark not only because it marks the lower limit of the prostate 2 but also because it indicates the level of the external urethral sphincter 8. Surrounding the prostate 2, like an orange skin, is the prostatic capsule 6.

Figure 2:
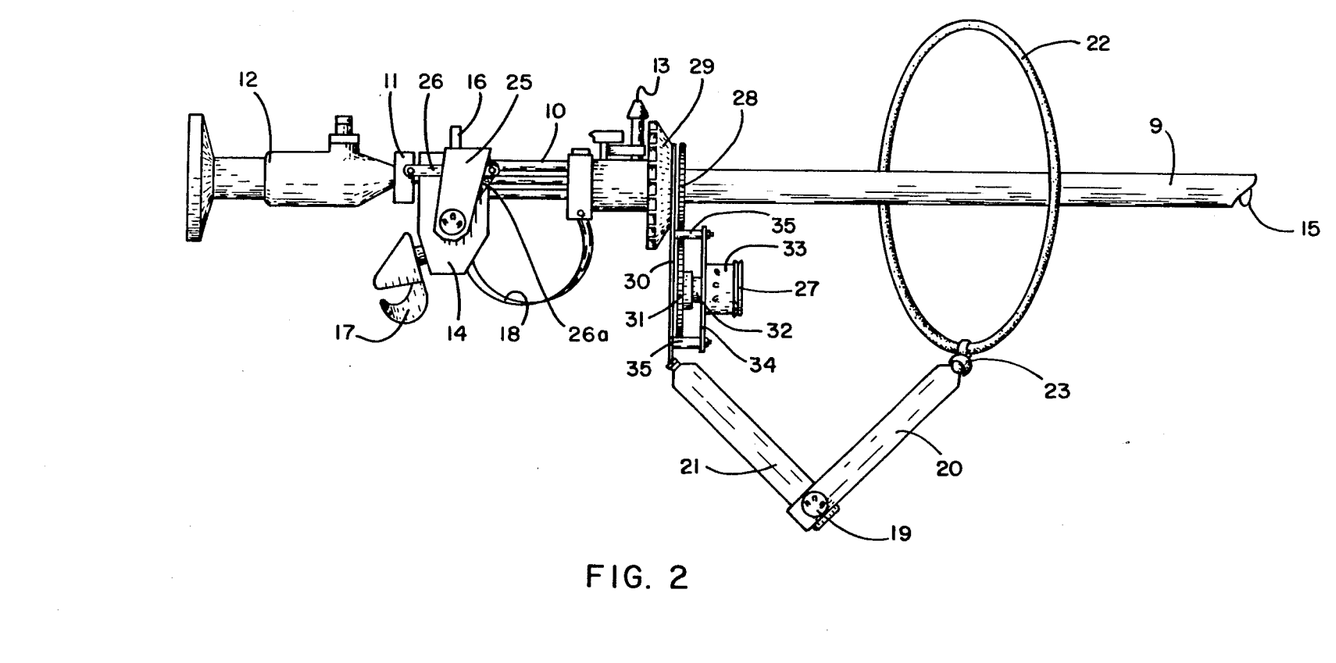
FIG. 2 is a view of the endoscope with additions necessary for the invention.

The endoscope in FIG. 2 is called resectoscope and is available from many sources. This one is manufactured by Statham Instruments Inc., 2330 Statham Blvd, Oxnard, Calif. 93030. Its two main parts are the resectoscope sheath 9 and the working element 10.

The working element 10 consists of a fixed part 11 and a moving part 14. The fixed part 11 helps to support the telescope 12 and provides and inlet 13 for irrigating fluid which when flowing keeps the operative field clear. The part that is movable 14 holds the cutting element 15 and has a socket 16 which connects to an external source (not shown) of high frequency current that is used to cut tissue and stop bleeding by coagulation. This movable part 14 also has a thumb grip 17 to push the cutting loop 15 forward and a spring 18 (U.S. Pat. No. 3,835,842) to bring the loop 15 back to its resting position.

Movements of the resectoscope shown in FIG. 2 are three. One is in an 'in and out' direction. Second is the movement of the cutting loop 15 'in and out' of the resectoscope sheath 9. The third movement is movement of the whole endoscope in a 'circular plane'. This is to be able to inspect and operate upon the organ all round starting from say the 1 O'clock position round in a clockwise direction to the 12 O'clock position.

Transducers are used to convert the above mentioned movements to digital data. In this particular model three potentiometers 19, 24, 27 each having a resistance of 0 to 150,000 ohms are used—one potentiometer for each of the above mentioned movements. As described below the body of each potentiometer is fixed to one part and the rotary moving contact of the potentiometer is fixed so that rotation of the moving contact occurs when the above mentioned movement occurs.

The first potentiometer 19 varies resistance with the 'in and out' movement of the endoscope. The body of the potentiometer 19 is fixed to one arm 20 and the moving contact to the other arm 21. Each arm 20, and 21 are equal in length to ensure linearity of resistance with distance travelled. The distal arm 20 is connected to a ring 22 with a ball and socket joint 23. This ring is fixed to the patients body (not shown) with adhesive tape.

For the second movement another potentiometer 24 is used. The body of this potemtiometer 24 is fixed to the moving part 14 of the working element 10 by a plate 25. The rotating contact of the potentiometer 24 is connected to the non moving part 11 of the working element 10 by two hinged flat metal pieces 26 and 26a. As the cutting loop 15 is moved in and out the resistance of the potentiometer 24 changes.

The third potentiometer 27 varies resistance with circular motion. To the resectoscope sheath 9 is attached a ring with teeth 28. This ring 28 is fixed to the resectoscope sheath flange 29. This ring moves round with circular movement of the resectoscope. Between this ring 28 and the resectoscope sheath flange 29 is a plate 30 that extends downward. There is a space between the ring 28 and the flange 29 so that this plate 30 does not move when the resectoscope moves in a circular plane, but always hangs down due to gravity. From this plate 30 are four spacers 35 that hold another plate 34 which is fixed to the body 33 of the potentiometer 27. To the moving part 32 of potentiometer 27 is fixed a toothed ring 31. This ring's teeth are enmeshed with the teeth of ring 28 which is above. This assembly hangs down always due to gravity but with the circular movement of the resectoscope the resistance of potentiometer 27 changes proportionately.

To interface with a computer analog signals have to be converted to digital numbers. Analog to digital converter (ADC) chips are readily available. Since most personal computers have ADC already built in, this is used in the present model. Such ADC are used to play games with joystick, paddles and push buttons.

The computer used is an Apple Computer, model IIe obtainable from Apple Computer Inc., 20525 Mariani Ave., Cupertino, Calif. 95014. Analog to digital conversion in the computer is accomplished by using a special integrated circuit chip IC NE 558 Quad Timer. Each game control (GC) input is part of an analog to digital conversion circuit that allows an analog resistance value to be converted (by software) to a digital quantity the IIe can handle. The resistor forms part of a simple 'R C' (resistor capacitor) circuit that sets the time constant of the IC NE 558 timer. When this timer is reset, by accessing GCRESET ($C070) bit 7 of each G C (game control) I/O (input/output) memory location becomes high (1) but will eventually become low (0) when the timer 'times out', that is, the period of time equal to the time constant for each of the four "R C" circuits has elapsed. (page 338, Inside the Apple IIe by Gary B. Little, published by Brady Communication Co., Inc., Bowie, Md., 20715).

The Apple IIe has four ADC (analog to digital converter) connected to the game port which are similar in concept to a dual slope ADC (analog to digital converter). A fixed 5 volt is connected to one end of a variable resistance. The output of the variable resistance has current which varies inversely with the resistance. This incoming current charges a capacitor until the charge becomes equal to a reference charge stored in a second capacitor. The amount of time for the input capacitor to become fully charged is proportional to the setting of the resistor in the game paddle or other device. There is a subroutine in the monitor which begins the sampling process and then checks the status of the ADC (analog to digital converter) every 10.8 microseconds. If the external resistance is near zero, the ADC is triggered very rapidly. With a maximum resistance of 150,000 ohms it can take up to 256 test periods or $256 \times 10.8 = 2.76$ milliseconds to determine the setting. (page 246-247 Apple Thesaurus by Aaron Filler, published by Datamost, 20660 Nordhoff St., Chatsworth, Calif., 91311—6152).

Figure 3:
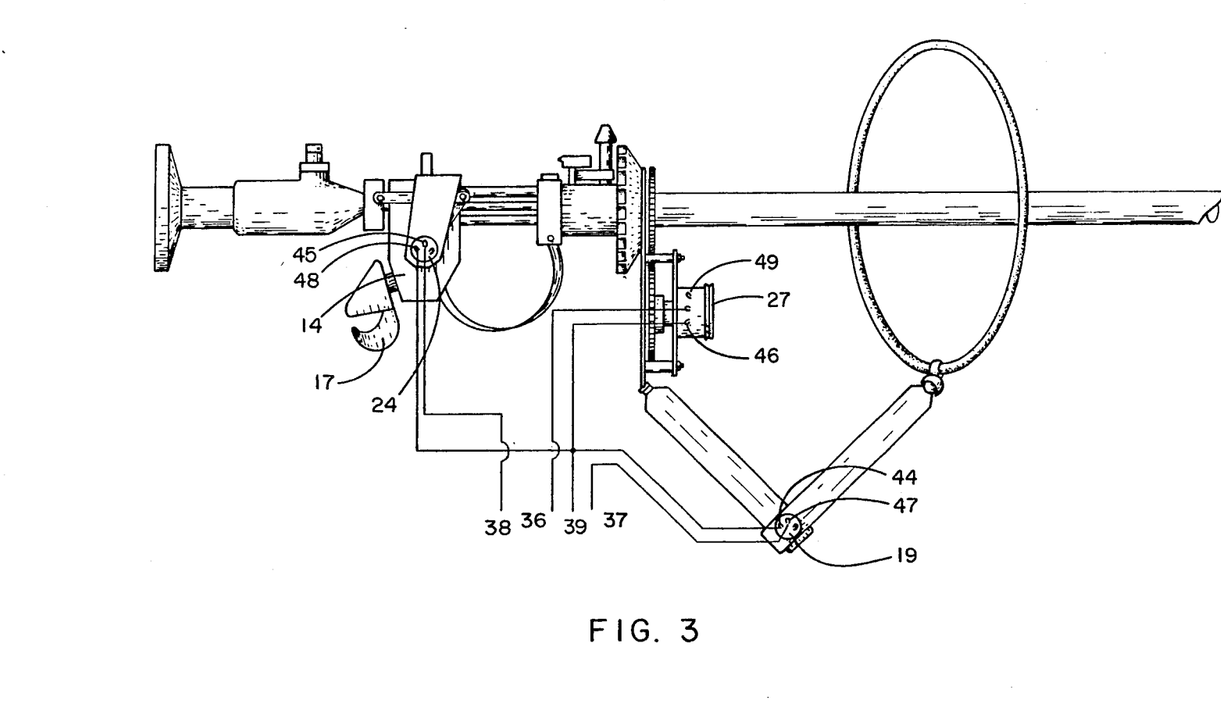
FIG. 3 is a view of the endoscope and in schematic form the wiring from the added components.
Figure 4:
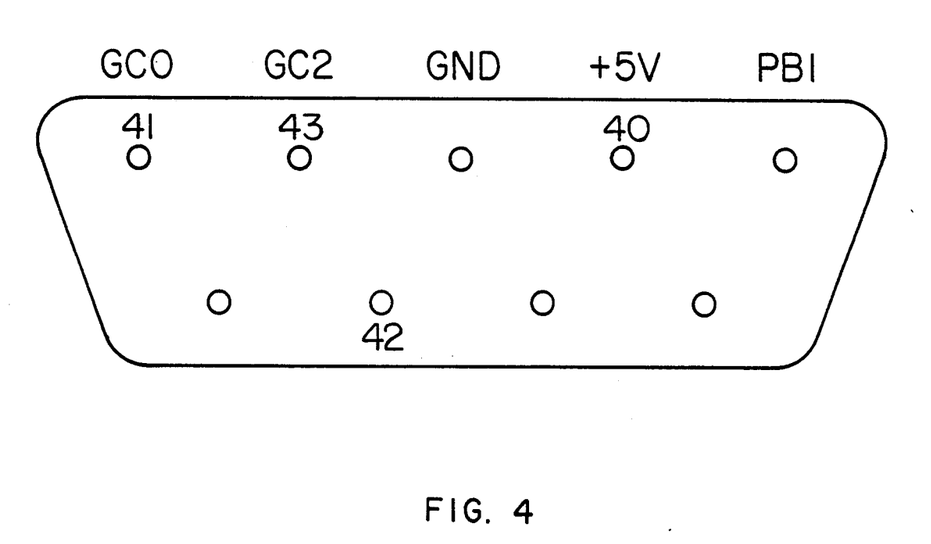
FIG. 4 is a view of the game input port of the Apple IIe computer.

FIG. 3 shows in a schematic form wiring from the said resectoscope potentiometers to the computer game control port FIG. 4. A +5 volts is supplied from 40 and is connected via wire 39 to one terminal 44, 48, 46 of each potentiometer. Potentiometer 19 transduces 'in and out' movement of the resectoscope and output of variaton is taken from 47 and goes out via wire 37 to connection 41 which is input of GC0 (Game control input number 0). Similarly output of potentiometer 24 which varies with movement of the cutting loop 15 is taken from terminal 45 via wire 38 to GC1 (game control number 1) input 42. Potentiometer 27 is for rotary movement and terminal 49 is connected to GC2 (game control number 2) input 43 via wire 36.

Figure 5:
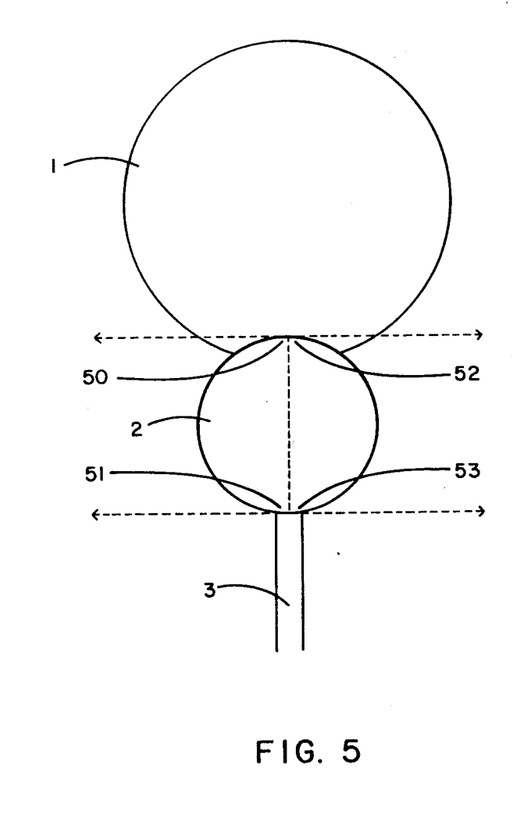
FIG. 5 is to show how the prostate is to be represented in graphic form.
Figure 6:
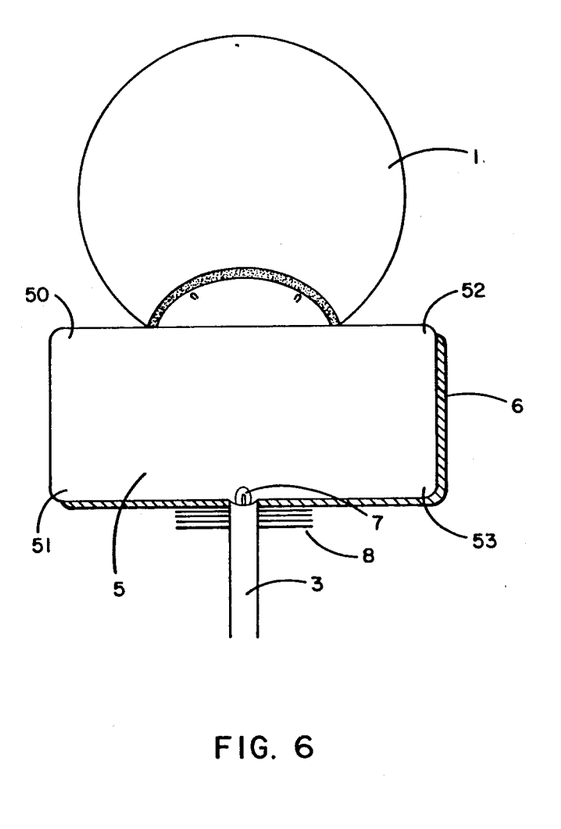
FIG. 6 is a view of the prostate opened out to enable graphic representation.

The method of displaying the prostate on the computer screen is shown in FIG. 5 and FIG. 6. The prostate is shown as if it has been cut open from the 12 O'clock position to its center and opened out in the form of a rectangle. The left side is 50, 51 and the right side 52, 53. The opened prostate as a rectangle is shown in FIG. 6. The visible part is the inside surface of the prostate 2. This inside surface is the prostatic urethra 5. The capsule 6 or outer boundary is deep to the surface.

Figure 7:
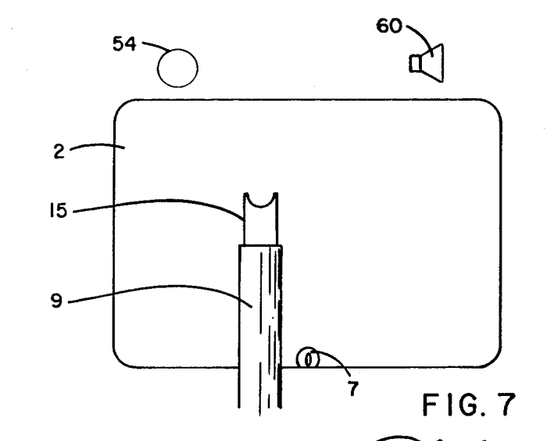
FIG. 7 shows the endoscope sheath and cutting element in relation to the graphic representation of the prostate.
Figure 8:
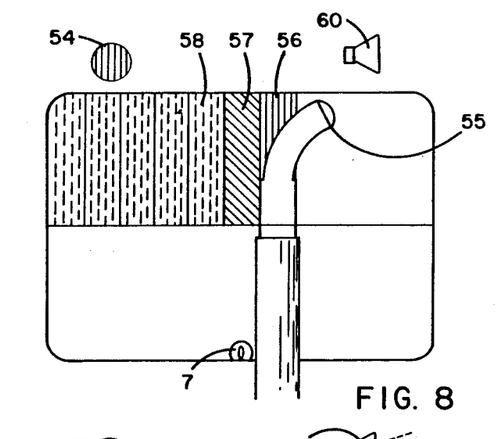
FIG. 8 is to show how the cutting of the prostate is represented in graphic form.
Figure 11:
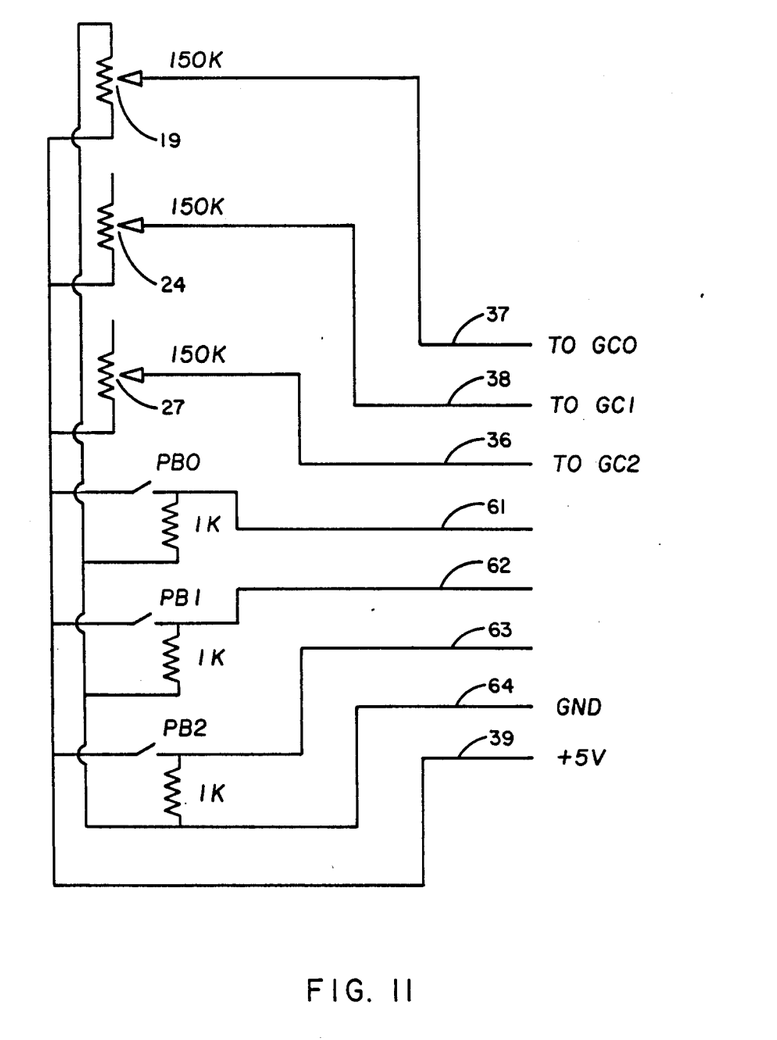
FIG. 11 shows the circuit diagram of the computer interface and the Apple IIe Game Input Port.

FIG. 7 shows the prostate 2 opened out as a rectangle. The resectoscope sheath 9 and cutting loop 15 are also seen. The said loop 15 and sheath 9 are seen on the computer screen to move up and down as it is moved by the surgeon. The loop 15 and sheath 9 together move sideways on the screen as it is rotated in a circular plane by the operating surgeon. In addition the loop 15 is shown to move in and out of the resectoscope sheath 9 exactly as it occurs during the surgery. The circle 54 becomes colored pink when the cutting current is about to be switched on by a foot switch and during the time it is on. To enable this, the switch PB0 (FIG. 11) 61, is coupled to the cutting current left foot switch (not shown) so that when this switch is depressed PB0 61 is first activated, FIG. 8 54, then as this switch is further depressed the cutting current switch is activated. As shown in FIG. 8 a part of the prostate being cut 55. The color deep to it changes to pink 56. To the left of this an additional slice of prostate was removed hence its color changed to green 57. Again from the left of this part 57 to the left edge, prostatic capsule 6 has been reached hence it is all given the final color of purple 58.

While cutting into the prostate 2 the capsule 6 can be easily recognized. As a slice of prostate is cut and casule has been reached in that part, a push button PB1 (FIG. 11) 62, coupled to a right foot switch, is switched on momentarily by the surgeon. This colors that part of the prostate purple on the computer screen indicating that in this portion capsule has been reached.

Figure 10:
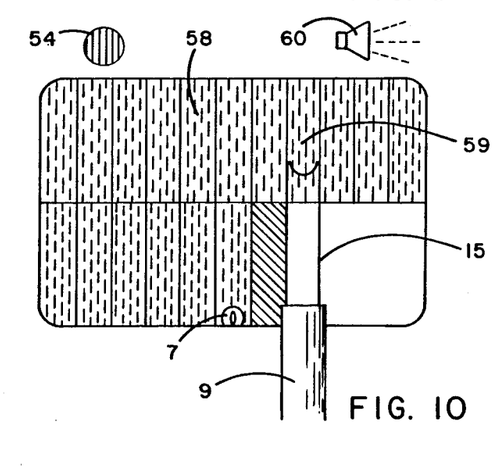
FIG. 10 shows alarm when cutting is about to be performed in an area where the safe limit has already been reached.

In FIG. 10 the distal half of the prostate is being resected. The cutting loop 15 is in a place where capsule has already been reached 59 and the cutting current is about to be switched on 54. Here there ia a danger of cutting the capsule and perforating it hence the alarm 60 sounds to alert the surgeon.

Figure 9:
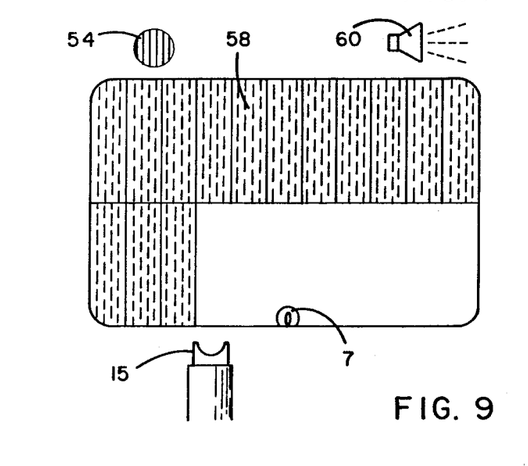
FIG. 9 shows representation of alarm when cutting is about to be performed beyond safe limits.

In FIG. 9 the resectoscope loop 15 is beyond the veru 7 and the cutting current foot switch is depressed activating switch PB0 61 first. The alarm 60 sounds alerting the surgeon before he further depresses the foot switch to activate the cutting current. Similarly the alarm will sound if the cutting loop 15 is above the bladder neck 6, the upper safe limit, and the cutting current is about to be switched on (not shown).

Computer software specifics vary with each type of computer. In general the computer is programed to do the following: First bladder 1, prostate 2, and urethra 3 are drawn on the screen as in FIG. 1. Then the prostate 2 is shown to open out to form a rectangle FIG. 5 and FIG. 6. The bladder 2 and urethra 3 disappear leaving a rectangle as in FIG. 7.

High resolution graphics is used. From shape tables in memory shapes of the end of the resectoscope sheath 9 and the end of the resectoscope cutting loop 15 are loaded. According to variations of current at computer input GC0, FIG. 11 37, these two shapes namely sheath 9 and loop 15 move together up and down on the screen. Combined readings from input GC0+GC1 37, 38 move the loop 15 in and out of the sheath 9. Sideways movement occur with variations to input GC2 36.

The upper limit of the rectangle is redrawn by bringing the loop 15 to the level of the bladder neck 4 and pressing right foot switch activating PB1. Similarly the lower limit is set by bringing the loop to the level of the veru 7 and again activating PB1 62. The upper and lower limits are set and assigned to variables in the computer. Setting these limits is followed by reading the surgery starting time. A seperate plug in card called Business Card has a clock. Time is read from this. This is obtainable from Street Electronics Corp., 1140 Mark Ave., Kartinteria, Calif. 93013. It is plugged in one of the plug in slots in the Apple IIe computer.

Digital data converted from inputs GC0 37, GC1 38, and GC2 36 are obtained by variables assigned to computer commands PDL(0), PDL(1), and PDL(2) respectively. These readings then help to move the sheath 9 and loop 15 as described.

Push button switch PB0 61 is coupled to the left foot switch that switches the cutting current. As soon as this switch PB0 61 is activated the position of the cutting edge of the loop 15 is read. Then three things are checked. Is this above the bladder neck 4, or is it below the veru 7, or is it in an area of capsule 6? If the answer is yes then an audible alarm sounds. If necessary it is easy to deactivate the cutting current. If the answer is no then the color over the area where this loop 15 moves is changed. A two dimensional array is formed representing plot positions of the area occupied by the prostate on the computer screen. When PB0 is activated and the loop 15 is moved, the position of the cutting edge of the loop 15 is read from PDL(0)+PDL(1) which gives the X axis position and from PDL(2) which gives the Y axis postion. While cutting switch PB0 is depressed wherever the loop 15 moves the color is changed. The number of this color is stored in the above mentioned array. When cutting is done over the same area again then the color is changed to the next color. Colors available are black, pink, green, blue, and purple.

Begining color is black. Then when the first cut is made the area traversed by the loop 15 becomes pink. After the second cut over the same area color changes to green. The third cut makes it blue. If another cut is made over the same area it becomes pink. Thus between the first and final colors three colors come in sequence—pink, green, blue, pink, green, blue, etc. When the capsule 6 is reached PB1 62 is depressed. This causes the color to change to the final color—purple. All this time numbers for colors are changed and stored in the array. The final color of purple holds special significance because when the cutting curent PB0 is on, one of the three things the computer checks is whether the location where the loop 15 traverses has the final color purple. If the answer is yes then the alarm sounds alerting the surgeon that the loop 15 is over capsule and cutting can cause perforation. At the end of the one look at the computer screen will tell whether all prostate has been completely removed or not. Purple color occupying the whole area indicates complete removal.

One of the computer subroutines is to read the X axis, Y axis, and color numbers at the location occupied by the loop 15 cutting edge. These numbers are stored in a sequential access file. This is to make a permenant record of events occurring during the surgery. Upper and lower limit positions will also be saved. Replay will be done by recalling these numbers and moving the loop 15 according to location indicated by the position numbers and color will change according to the color number.

Thus, according to this invention the endoscopic examining and treatment procedures will become much safer.

What is claimed is:

1. In an endoscope of the type having a main body including a sheath, a working element slidingly disposed within said sheath, and a cutting element mounted on the distal end of said working element, the improvement comprising:
    (a) means for attaching said endoscope to the body of a patient to provide a fixed reference point; and
    (b) means for measuring the position of said cutting element in relation to said fixed point as the cutting element is moved about the area being explored.

2. The endoscope of claim 1 wherein said measuring means includes:
    (a) means for measuring the longitudinal movement of said main body relative to said fixed point;
    (b) means for measuring the rotation of said main body in relation to said fixed point; and
    (c) means for measuring the longitudinal movement of said cutting element in relation to said main body.

3. The endoscope of claim 1 wherein said measuring means includes means for converting the measurements being made into electrical signals and using said electrical signals in a display means to show the position and movement of said cutting element.

4. The endoscope of claim 3 wherein said display means includes signal processing means to process said electrical signals and to produce display signals representing the position and movement of said cutting element on a display screen.

5. The endoscope of claim 3 further including means operatively connected to said measuring means and said display means for determining and measuring the limits of the area being examined and for generating and displaying a schematic representation of said area including said limits so that the position of said cutting element in relation to said area can be monitored.

6. The endoscope of claim 5 further including alarm means operatively connected to said endoscope, and means for activating said alarm means when said cutting element transgresses said limits of the area being examined and treated.

7. The endoscope of claim 5 further including disabling means operatively connected to said endoscope for disabling said cutting element when said limits of the area being examined are transgressed by said cutting element.

8. The endoscope of claim 5 further including data storage means for recording the position and movement of said cutting element in relation to the area being examined and treated for future replay.

9. The endoscope of claim 5 further including means for indicating on said schematic representation of the area being examined those parts thereof which have been affected by said cutting element and those parts which remain unaffected.

10. A system for monitoring and displaying on a display screen the movement of an endoscope in relation to the area being examined and treated comprising:
    (a) an endoscope including a distal end portion capable of being inserted into the body of a patient for examination and treatment;
    (b) means for attaching said endoscope to said patient's body to provide a fixed reference point;
    (c) means for measuring the limits of the area being examined and treated in relation to said reference point;
    (d) means for measuring the position of said distal end portion of said endoscope in relation to said reference point; and
    (e) means associated with each said measuring means for generating and displaying a representation of the area being examined and treated including said limits and indicating the position of the distal end portion of said endoscope in relation to such area.

11. The system of claim 10 wherein said display means include:
    (a) means associated with each of said measuring means for converting said measurements into electrical signals;
    (b) signal processing means to process said electrical signals and to produce display signals representing the limits of the area being examined and the position of said distal end portion of said endoscope in relation to such area; and
    (c) a display screen for displaying a representation of the area being examined and the position of the distal end portion of said endoscope in relation to said area using said display signals from said signal processing means.

12. The system of claim 10 further including alarm means operatively connected to said endoscope, and means for activating said alarm means when the limits of the area being examined are transgressed by said distal end portion of said endoscope.

13. The system of claim 10 further including data storage means for recording the position and movement of the distal end portion of said endoscope in relation to the area being examined and treated for future replay.

14. A process for monitoring the movement of an endoscope in relation to an area being examined not treated comprising:

(a) attaching said endoscope to the patient's body to provide a fixed reference point;

(b) inserting the distal end of the endoscope into the area to be examined and treated;

(c) measuring the limits of the area being examined and treated in relation to said reference point;

(d) measuring the position of the distal end of said endoscope in relation to said reference point;

(e) converting each of said measurements into electrical signals;

(f) using said electrical signals to generate graphic representation of the area being examined including said limits and to indicate the position and movement of said distal end of said endoscope in relation to such area.

15. The process of claim 14 further including:

(a) comparing the position of the distal end of said endoscope to the limits of the area being examined;

(b) activating an alarm when said limits are transgressed by the distal end of said endoscope.

16. The process of claim 14 further including recording the position and movement of the distal end of said endoscope in relation the area being examined and treated for future replay.

17. The process of claim 14 wherein said endoscope includes a cutting element on said distal end portion of said endoscope, said process further including:

(a) measuring the position and movement of the cutting element in relation to the area being examined and treated;

(b) converting said measurements into electrical signals; and (c) using said electrical signals to indicate on said representation the areas affected by said cutting element and the areas which remain unaffected.

18. The process of claim 17 further including:

(a) comparing the position of said cutting element to the limits of the area being examined and treated; and (b) disabling said cutting element when said limits are transgressed by said cutting element.

* * * * *

UNITED STATES PATENT AND TRADEMARK OFFICE
CERTIFICATE OF CORRECTION

PATENT NO. : 4,742,815

DATED : May 10, 1988

INVENTOR(S) : Champil A. Ninan et al.

It is certified that error appears in the above-identified patent and that said Letters Patent is hereby corrected as shown below: On the title page:

On page 1, the address of the Inventors should be changed to:

-- 453 Morningside Drive

Fayetteville, North Carolina 28311 --.

Column 2; line 49, delete "ditital" and insert therefor -- digital --.

Signed and Sealed this

Eighth Day of November, 1988

Attest:

DONALD J. QUIGG

Attesting Officer

Commissioner of Patents and Trademarks